United States Patent [19]

Ando et al.

[11] 4,177,121

[45] Dec. 4, 1979

[54] METHOD OF PRODUCING N-FORMYLAMINE

[75] Inventors: Wataru Ando, Sakura; Kazuo Watanabe, Kiryu, both of Japan

[73] Assignee: K. K. Pollution Preventing Research Laboratory, Tokyo, Japan

[21] Appl. No.: 926,717

[22] Filed: Jul. 21, 1978

[30] Foreign Application Priority Data

Jul. 22, 1977 [JP] Japan .................................. 52/87304

[51] Int. Cl.² .............................................. B01J 1/10
[52] U.S. Cl. ............................................. 204/158 R
[58] Field of Search .................................. 204/158 R

[56] References Cited

PUBLICATIONS

Foote et al., Tetrahedron Letters, No. 29 (1968), pp. 3267–3270.

Primary Examiner—Howard S. Williams
Attorney, Agent, or Firm—Fitzpatrick, Cella, Harper & Scinto

[57] ABSTRACT

This invention provides a method of producing N-formylamine by photosensitized oxygenation of aldehyde-amine mixture. According to this invention, N-formylamine can be produced directly by photosensitized oxygenation of an aldehyde-amine mixture without separating intermediate enamine. In this invention, enamine is not used as a reactant, i.e. starting material, but a mixture of the aldehyde and amine is used as a reactant.

7 Claims, No Drawings

METHOD OF PRODUCING N-FORMYLAMINE

BACKGROUND OF THE INVENTION a. Field of the Invention

This invention relates to a method of producing N-formylamine by photosensitized oxygenation of aldehyde-amine mixture whereupon carbonyl transformation from aldehyde to amine occurs.

b. Description of the Prior Arts

There have been known several methods of producing N-formylamine since the late period of 1950. Those conventional techniques are as follows:

(1) N-formylamine is produced by the reaction of amine with carbon monoxide at a high temperature and pressure in the presence of a metal catalyst of transition state.

(2) N-formylamine is produced by the reaction of the corresponding amine with formic acid or chloral.

(3) Christopher S. Foote and John Wei-Ping Lin disclosed in Tetrahedron Letters No. 29, pp. 3267–3270, 1968 that the reaction of aldehyde enamines with singlet oxygen affords corresponding ketones and N-formylamine as carbon-carbon cleavage products in quantitative yields.

In this case, however, firstly the enamine should be prepared by reacting aldehyde with amine. Then, the resulted enamine should be separated to be used for the reaction as above mentioned. Therefore, this method includes more steps than the method of the present invention hereinafter mentioned. Also, this method is not suitable to an unstable enamine to be scarcely separated. It is significant that N-formyl piperidine or morpholine could be produced directly by photosensitized oxygenation of aldehyde-amine mixture under mild condition, without separating intermediate enamine.

Dimethylformamine(DMF) and dimethylsulfoxide(DMSO) are high polar aprotic solvents, and are used widely. DMF cannot, however, be used as a solvent at a high temperature reaction about 200° C., because of its boiling point comparatively not higher than N-formylpiperidine (VI) and N-formylmorpholine (III).

Said compounds (III) and (VI) are the homologues of DMF and have almost the same properties concerning chemical property or capability of dissoluting gases and inorganic substance. However, the boiling points of the compounds (III) and (VI) are considerably higher than that of DMF so that the compounds (III) and (VI) are ideal as excellent and non-volatile solvents.

It is important for a solvent to be used that the temperature range of liquid state thereof is broad.

The temperature range of liquid state of (VI) and (III) is wider than that of DMF by about 40° C. This is evident referring to the following table.

Table I

| Amide Physical property | $HCNMe_2$ $\parallel$ $O$ | $HCN$ $\parallel$ $O$ ⬡ (VI) | $HCN$ $\parallel$ $O$ ⬡O (III) |
|---|---|---|---|
| Boiling point | 153° C. | 222° C. | 120° C./15mm |
| Melting point | −60 | −31 | 22 |
| Temperature range of liquid state | 213° | 253° | about 250° |

In addition, the characteristic and important property of the compounds (VI) and (III) is the high capability of solubilizing high polymers. The compounds (III) and (VI) are practically used as excellent solvents in the chemical industry of high polymers. The compounds (III) and (VI) are very soluble in hexane as well as water, and easily obtainable by distillation in pure and anhydrous state. The advantage of the compounds (III) and (VI) over DMF is the fairly slower absorption of moisture from atmosphere. Thus, it is understood that the compounds (III) and (VI) are very excellent high polar aprotic solvents and applicable to wider variety than DMF. Therefore, it is significant to synthesize simply and economically the compounds (III) and (VI).

SUMMARY OF THE INVENTION

This invention relates to a method of producing N-formylamine accompanied with a lower aldehyde or ketone of by-product by photosensitized oxygenation of an approximately equivalent mixture of an aldehyde having at least one α-hydrogen and an aliphatic or heterocyclic amine whereupon carbonyl transformation from aldehyde to amine occurs. In other words, in this invention N-formylamine can be produced directly by photosensitized oxygenation of an aldehyde-amine mixture without separating intermediate enamine.

The feature of this invention, therefore, is in that N-formylamine is obtained by photosensitized oxygenation by not using enamine as a reactant i.e. starting material, but using a mixture of said aldehyde and amine as the reactants.

The other feature of the invention is mentioned as follows.

By photosensitized oxygenation of a mixture of long chain non-branched aldehyde having at least one α-hydrogen and a large excess of aliphatic or heterocyclic amine, the carbonyl transformation reaction as above mentioned can occur to produce N-formylamine with the first by-product aldehyde.

It is notable, however, that said first by-product aldehyde is the homologue having less carbon numbers than the starting aldehyde by 1.

Next, the first by-product aldehyde is mixed with an excess of said starting amine, and followed by photosensitized oxygenation of this mixture to produce the same N-formylamine with the second by-product aldehyde.

Then, using the mixture of said second by-product aldehyde and an excess of said starting amine, the same photosensitized oxygenation is carried out to produce the same N-formylamine with the third by-product aldehyde. Each relation of the second by-product aldehyde to the first by-product aldehyde, and the third by-product aldehyde to the second by-product aldehyde is the same manner as mentioned hereinbefore in connection with the carbon numbers.

Therefore, if progressively these reactions being repeated, the same N-formylamine accumulates, and resulting in obtaining the N-formylamine in more than 100% yield on basis of the starting aldehyde. That is to say, this effective carbonyl transformation to amine includes the reproduction of aldehyde.

The present invention, in particular, relates to a direct method of producing N-formylpiperidine or N-formylmorpholine by photosensitized oxygenation of a mixture of aldehyde having α-hydrogen and piperidine or morpholine.

Regarding the direct method of producing N-formylamine by photosensitized oxygenation of aldehyde-amine mixture, there is not relevant prior arts to the best knowledge of the present inventors.

It is, therefore, a primary object of the present invention to provide a novel method of producing N-formylamine by photosensitized oxygenation of aldehyde-amine mixture.

The other object of the invention is to provide a simple method of producing industrially useful aprotic solvent such as N-formylpiperidine or N-formylmorpholine by photosensitized oxygenation of aldehyde-piperdine or morpholine mixture wherein recyclization process being involved.

The foregoing objects, other objects as well as the reaction to take place in the method of the present invention will become more apparent and understandable from the following detailed description of the invention, when read in connection with several preferred examples thereof.

DESCRIPTION OF THE PREFERRED EMBODIMENT

In order to enable those persons skilled in the art to readily reduce the present invention into practice, the following preferred examples are presented. It should, however, be noted that these examples are merely illustrative and not restrictive, and that any change and modification may be made by those skilled in the art in respect of the various reaction conditions as mentioned in the foregoing, without departing from the spirit and scope of the present invention as set forth in the appended claims.

Hereinafter, examples are mentioned. In every examples, the reaction temperature is at a temperature below the boiling point of each aldehyde to be used.

1. First Part

Mixture of α-phenylpropionaldehyde (I, 1 equiv.) and morpholine (II, 1.2 equiv.) in pyridine was irradiated by 500 W tungsten lamp with oxygen bubbling for 40 min. in the presence of hematoporphyrine as sensitizer. The solution took up about 1.2 equivalent of oxygen. Solvent evaporation followed by glpc analysis gave N-formylmorpholine (III) in 70% yield accompanied with acetophenone (IV, 64%). Also the reaction of (I) and piperidine (V) gave N-formylpiperidine (VI) in 68% yield on the basis of (I). Glpc means gas liquid participation chromatography.

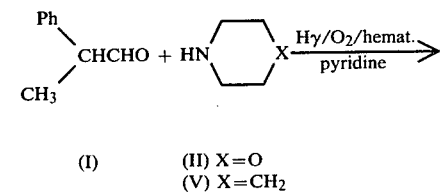

(I)   (II) X=O
      (V) X=CH$_2$

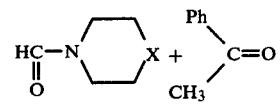

(III) 70%   (IV) 64%
(VI) 68%    64%

Appropriate control experiments indicated that the sensitizer, oxygen, and light were all necessary for these reactions. Products were characterized by spectroscopic and gas chromatographic comparisons with those of authentic samples. Results for various aldehyde and amine were summarized in Table II.

Table II

Yields of N-formylamines in the reactions of aldehyde-amine mixture with singlet oxygen.

| Aldehyde | Amine | N-formylamine | Yield (%) |
|---|---|---|---|
| Ph\CHCHO/CH$_3$ | HN⟨ ⟩O | HC(=O)—N⟨ ⟩O | 70 |
| Ph\CHCHO/CH$_3$ | HN⟨ ⟩ | HC(=O)—N⟨ ⟩ | 68 |
| Ph\CHCHO/CH$_3$ | HN(CH$_2$CH$_3$)$_2$ | HC(=O)—N(CH$_2$CH$_3$)$_2$ | 67 |
| Ph\CHCHO/CH$_3$ | HN(CH$_3$)Ph | none[a] | — |
| (CH$_3$)$_2$CHCHO | HN⟨ ⟩O | HC(=O)—N⟨ ⟩O | 60 |
| CH$_3$CHO | HN⟨ ⟩O | HC(=O)—N⟨ ⟩O | 45 |
| PhCHO | HN⟨ ⟩O | none[a] | — |

[a]Aldehyde and amine were recovered in quantitative yield.

As shown in Table II, in case of the reactions with benzaldehyde or N-methylaniline, N-formylamine was not obtained, and the starting aldehyde and amine were only recovered under the reaction conditions. It may be important that aldehydes should contain at least α-hydrogen for these carbonyl transformation reactions.

Considering that this reaction proceeded only in the combination of aldehydes containing α-hydrogen and alkylamines, or heterocyclic amines the carbonyl transformation seems to involve the formation of enamine as intermediate. (Scheme I) It is significant that the N-formylamine and ketone are obtained without using enamine as reactant. Formally, the formation of N-formylamine was taken to be carbonyl transformation from aldehyde to amine by photosensitized oxygenation.

Scheme I.

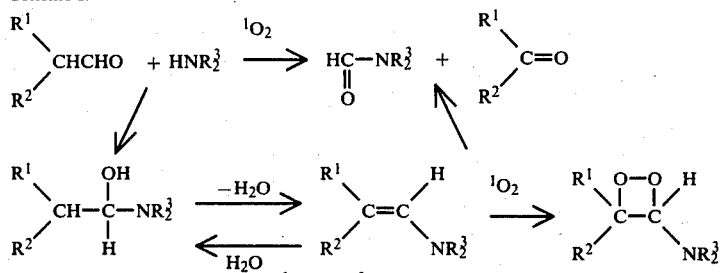

In the above formula, $R^1$ and $R^2$ are hydrogen, alkyl or allyl; $R^3$ is alkyl or heterocyclic $^1O_2$ is singlet oxygen and $HNR_2^3$ is amine.

2. Second Part

In the aspect of synthetic method, the yields of N-formylation product are of much importance. When an excess of amine is used, the N-formylamine yields more than 100% on the basis of aldehyde. (Scheme II)

Scheme II.

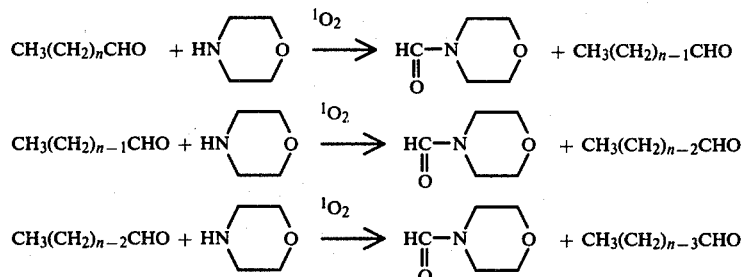

Mixture of propionaldehyde (VII, 2.73 mmole) and morpholine (5.76 mmole) in methylene chloride was irradiated for 90 min with oxygen bubbling in the presence of methylene blue. N-formylmorpholine was obtained in 103% yield on the basis of (VII), as expected. Further, mixture of propionaldehyde (2.73 mmole) and morpholine (11.52 mmole) gave N-formylmorpholine in 145% yield. When n-octylaldehyde (VIII) was used, the yield of N-formylmorpholine went up to 272% by irradiation for 240 min. (Table III.) Also the reaction of mixture of (VIII) and piperidine affords the same results. For example, N-formylpiperidine was obtained in 282% yield for 1.29 mmole of (VIII) and 20.5 mmole of (V). Also, N-formylpiperidine was obtained in 281% yield for the mole ratio of piperidine (V) to n-octylaldehyde (VIII) being 9 for 280 min.

These results were summarized in Table III.

Table III.

| Yields of N-formylmorpholine (III) in mixture of aldehyde (A) and morpholine (B). | | | |
|---|---|---|---|
| Aldehyde (A) | Mole ratio (B) / (A) | Irrdn. time (min) | Yield of (III) (%) |
| $CH_3CH_2CHO$ | 1.05 | 90 | 46 |
| $CH_3CH_2CHO$ | 2.10 | 90 | 103 |
| $CH_3CH_2CHO$ | 4.20 | 90 | 145 |
| $CH_3CH_2CHO$ | 6.30 | 180 | 162 |
| $CH_3(CH_2)_2CHO$ | 4.90 | 90 | 109 |
| $(CH_3)_2CHCHO$ | 5.20 | 90 | 35 |
| $CH_3(CH_2)_6CHO$ | 8.90 | 90 | 213 |

Table III.-continued

| Yields of N-formylmorpholine (III) in mixture of aldehyde (A) and morpholine (B). | | | |
|---|---|---|---|
| Aldehyde (A) | Mole ratio (B) / (A) | Irrdn. time (min) | Yield of (III) (%) |
| $CH_3(CH_2)_6CHO$ | 8.90 | 240 | 272 |

The reaction process of this invention which includes reproduction of aldehyde can be used as a useful synthetic method of N-formylamine.

What we claim is:

1. A direct method of producing an N-formylamine and a lower oxo by-product comprising conducting a photosensitized oxygenation of a reaction mixture, in the presence of a solvent therefor, said mixture comprising (a) an aldehyde having at least one α-hydrogen and at least two carbon atoms, (b) an aliphatic or heterocyclic secondary amine and (c) a sensitizer, whereby a carbonyl transfer to the secondary amine occurs which results in a reduction in the carbon atoms of the aldehyde.

2. The method of claim 1 in which the aldehyde is a long chain non-branched aldehyde having at least one α-hydrogen and at least three carbon atoms, the mole ratio of said secondary amine to said aldehyde is greater than 2:1 and the step of repeating at least once the photosensitized oxygenation of the reaction mixture containing the lower by-product and unreacted secondary amine, whereby enhanced yields of N-formylamine are formed as a result of the progressive reduction in the chain length of the aldehyde upon repetition of the process.

3. The method according to claim 2 in which said amine is morpholine and said aldehyde is an aliphatic aldehyde having at least three carbon atoms.

4. The method according to claim 2 in which said amine is piperidine and said aldehyde is an aliphatic aldehyde having at least four carbon atoms.

5. A method according to claim 1 in which said amine is morpholine.

6. A method according to claim 1 in which said amine is piperidine.

7. A method according to claim 1 in which said amine is diethylamine.

* * * * *